United States Patent [19]
Wai

[11] Patent Number: 6,082,173
[45] Date of Patent: Jul. 4, 2000

[54] METHOD AND APPARATUS FOR PILE DRIVING

[76] Inventor: Yee Kong Wai, 18-3A, Jalan Pandan 3/7, Pandan Jaya, Kuala Lumpur, Malaysia, 55100

[21] Appl. No.: 09/153,549

[22] Filed: Sep. 15, 1998

[30] Foreign Application Priority Data

Sep. 15, 1997 [MY] Malaysia .............. PI9704268

[51] Int. Cl.[7] .................................. G01N 3/30
[52] U.S. Cl. .......................... 73/12.13; 73/12.01
[58] Field of Search ................ 73/12.01, 12.06, 73/12.09, 12.13

[56] References Cited

U.S. PATENT DOCUMENTS

| | | | |
|---|---|---|---|
| 2,496,420 | 2/1950 | Stern | 73/12.13 |
| 2,531,388 | 11/1950 | Black | 73/12.13 |
| 3,879,982 | 4/1975 | Schmidt | 73/12.01 |
| 3,946,598 | 3/1976 | Towne et al. | 73/12.13 |
| 4,313,337 | 2/1982 | Myint | 73/12.13 |
| 4,359,890 | 11/1982 | Coelus | 73/12.13 |
| 4,531,400 | 7/1985 | Nevel | 73/12.13 |

OTHER PUBLICATIONS

British Standard Code of practice for Foundations (BS 8004: 1986). British Standards Institution: pp. 84–109, 1986.
Bowles, Joseph E. "Foundation Analysis and Design"; 4th edition, McGraw–Hill Book Company, 1988, Chapter 17, pp. 785–820.

*Primary Examiner*—Max Noori
*Attorney, Agent, or Firm*—Merchant & Gould P.C.

[57] ABSTRACT

A method and apparatus for estimating the load-bearing of a pile comprising (a) constructing a scaled-down model pile apparatus which has been reduced to a size that may be accommodated within an indoors facility according to a calculated scaled-down ratio; (b) subjecting said model pile apparatus to impact load tests to obtain dynamic measurements; and (c) correlating the dynamic measurements from said tests to said pile.

20 Claims, 5 Drawing Sheets

IMPACT LOAD MODEL

PILE DRIVING MODEL
(INVERTED DIAGRAM)

PROTOTYPE

MODEL

METHOD AND APPARATUS FOR PILE DRIVING

FIELD OF INVENTION

This invention concerns a new method for estimating load-bearing capacity of piles wherein the method is based on a model which has been scaled-down to a size small enough for an indoors facility measurement whereby the measurements may be employed in a mathematical formula to calculate and predict the load-bearing capacity of prototype or actual pile. A model pile apparatus devised for the method is also disclosed.

BACKGROUND OF INVENTION

There are a few major categories of foundation pile: driven pile, bored pile, injected pile. etc. This invention concerns only the first category, i.e. the driven pile. In the foundation construction industry, the most important aspect of a pile to a foundation engineer is the load-bearing capacity of the pile, i.e. how much load the pile may bear with respect to the building or structure to be built on the foundation.

Foundation engineers are engaged to design and choose pile types as laid down by the design requirements or standards (such as the British Standard BS 8004:1986). The foundation design is normally made after taking into consideration the columnar transferred load weight, soil type and conditions, piling system and pile design. Since soil type is an existing condition and the columnar transferred load has been predetermined in the design, the engineer may only advise on the two remaining variable factors, i.e. (i) pile design and (ii) piling system. In the present invention the piling system is the pile driving system.

For example, if the proposed pile is calculated to impose an estimated load of 300 tonnes via a structural column above the pile, the foundation engineer may assign a safety factor of 2 (SF=2, or twice the load on the pile, depending on the method of calculation), thus 2×300 tonnes=600 tonnes is the load the pile to be designed or chosen must be able to bear or support.

Foundation engineers then conduct tests on actual piles at a site based on that pile design. The piles are driven into the soil by hammer blows. Certain methods of calculations such as the Dynamic Pile Formulae, are used to predict the load-bearing capacity of the pile for a certain depth of penetration.

The prototype pile may then be statically and/or dynamically tested at-site to ascertain its load-bearing behaviour. This is a costly and time-consuming process.

As in the above example, if the field test shows that the (soil) resistance, R, is less than 600 tonnes, the pile design is considered to have failed and a new pile design is then sought and the process is repeated. The conditions at site, equipment used and current methods further make it impossible for an accurate prediction or measurement that is acceptable to a design requirement.

Dynamic Pile Formulae. For centuries, engineers have relied upon the number of hammer blows per unit of pile penetration to estimate the load-bearing capacity of the driven pile. Engineers have equated the hammer energy to the work done advancing the pile against the soil resistance.

There are many formulas used to determine the capacity of the piles driven into the soil. Theoretical and semi-empirical formulas are derived to express this relationship between energy and work. These equations are generally known as Dynamic Pile Formulae which is derived from Newton's Second Law of Motion and which are the most widely accepted formulas to determine the load-bearing capacity for driven piles.

The model common to all the simple Dynamic Pile Formulas is illustrated in FIG. 1 as $$Wh = Rs$$

or $$R = \frac{Wh}{s}$$

wherein $R$ = soil resistance
$W$ = hammer weight
$h$ = hammer stroke
$s$ = permanent set.

This basic dynamic pile-capacity formula, which is also termed rational pile formula, depends on impulse-momentum principles and nearly all the dynamic pile formulas currently in used are based on this equation. [See, for example, Joseph E. Bowles (1988), *Foundation Analysis and Design*, 4th ed., McGraw-Hill, p. 791].

Some of the specific formulas derived from the basic formula, in order to improve the reliability of predictions on the pile capacity by making various assumptions, each giving a different value of pile capacity, are given in the following table [Bowles, p. 794]:—

TABLE I

Various Dynamic Pile formulas

Danish formula [Olson and Flaate (1967)] (use SF = 3 to 6)

$$P_u = \frac{e_h E_h}{s + C_1}; \quad \text{wherein } C_1 = \sqrt{\frac{e_h E_h L}{2AE}}$$

Eytelwein formula (use SF = 6) [Chellis (1961)]

$$P_u = \frac{e_h E_h}{s + 0.1\left(\frac{W_p}{W_r}\right)}$$

Modified ENR (Engineering News-Record (1965)) (use SF = 6)

$$P_u = \frac{1.25 e_h \cdot E_h}{s + 0.1} \cdot \frac{W_r + n^2 W_p}{W_r + W_p}$$

Hiley Formula (1930)

$$P_u = \frac{e_h W_r h}{s + \frac{1}{2}(k_1 + k_2 + k_3)} \cdot \frac{W_r + n^2 W_p}{W_r + w_p}$$

wherein
$P_u$ = ultimate pile capacity, F.
$A$ = pile cross-section area, $L^2$.
$E$ = modulus of elasticity, $FL^{-2}$.
$e_h$ = hammer efficiency.
$E_h$ = manufacturers' hammer-energy rating, FL.
$h$ = height of all of ram, L.
$k_1$ = elastic compression of capblock and pile cap and is a form of $P_u L/AE$, L.
$k_2$ = elastic compression of pile and is of a form of $P_u L/AE$, L.
$k_3$ = elastic compression of soil, also termed quake for wave-equation analysis, L.
$L$ = pile length, L.
$n$ = coefficient of restitution.
$s$ = amount of point penetration per blow, L.
$W_p$ = weight of pile including weight of pile cap, driving shoe, and cap block (also includes anvil for double-acting steam hammers), F.
$W_r$ = weight of ram (for double-acting hammers include weight of casing), F.

Each of the formulas has their own respective advantages. For example, the modified ENR formula is thought to be reasonably valid over the entire range of load test. The Hiley formula is found to be with the least statistical deviation or highest statistical correlation [Bowles, p. 802]. The British Standard, BS 8004:1986, cited the Hiley formula as one of the more reliable and is probably the most commonly used in Britain.

Although dynamic formulas have been widely used to predict pile capacity, more accurate means is needed to determine when a pile has reached a satisfactory load bearing value other than by simply driving it to some depth predetermined by the formulas. This is because driving the pile to a predetermined depth may or may not obtain the required bearing value due to normal soil variation both laterally and vertically. [Bowles, ibid.] It is generally accepted that the dynamic formulas do not provide very reliable predictions but are continued to be used for lack of at better method.

There is therefore a need for a better method for accurately predicting a pile's load-bearing capacity. Due to the harsh external environment at foundation construction sites, it would be desirable if the pile capacity instrumentation and measurements could be conducted within an indoors facility such as in a geotechnical laboratory. The physical dimension limitations of an indoors facility means that the actual dimensions of the pile is preferably be scaled-down so that the pile and its requisite instrumentation or measurement means may be accommodated within the indoors facility.

Such a proposed scaled-down pile model will need a mathematical relationship in order to correlate its values to the pile's values so that the model may be used as an industrial application in estimating the capacity of a pile.

In this specification, the meaning of the words "prototype pile", "actual pile" and "pile" have been used interchangeably in view of the same physical characteristics of the piles when correlated to a model pile described herein.

SUMMARY OF INVENTION

The present invention provides for a method for estimating the load-bearing of a pile comprising (a) constructing a scaled-down model pile apparatus which has been reduced to a size that may be accommodated within an indoors facility according to a calculated scaled-down ratio; (b) subjecting said model pile apparatus to impact load tests to obtain dynamic measurements; and (c) correlating the dynamic measurements from said tests.

In one preferred embodiment the present invention provides a method wherein the correlation step uses a formula derived from the impact load theory.

In one preferred embodiment, the formula used in the present invention, is the Impact Load Formula:

$$P = W\left[1 + \sqrt{1 + \frac{2hAE}{WL}}\right] \quad \text{Formula I}$$

wherein $P$ = impact load on pile, tonnes;
$W$ = weight of impact mass, equivalent to weight of ram, tonnes;
$h$ = stroke, m;
$L$ = length of pile, m;
$A$ = cross sectional area pile, m²;
$E$ = Young's modulus of pile, tonnes/m²;

or any suitable derivative of Formula I to estimate the load-bearing of said pile.

Preferably, the derived Formula I used is $$R = \sqrt{\frac{2AEWh}{L}} \quad \text{Formula II}$$

wherein $R$ = soil resistance load or end load-bearing, tonnes;
$h$ = stroke, m;
$A$ = cross sectional area pile, m²;
$E$ = Young's modulus of pile, tonnes/m²;
$L$ = length of pile, m;
$W$ = weight of impact mass, equivalent to weight of ram, tonnes.

A preferred scaled-down ratio of prototype:model is in the range of x:1 where $1 \leq x \leq 100$. The most preferred ratio is 25:1.

In one preferred embodiment of the method according to the present invention, the scaled-down model pile apparatus further comprises a model pile and hammer weight, said model pile being provided with (i) means to gauge the strain exerted on said model pile upon being hit by the hammer weight, and (ii) means to measure the velocity of the stress wave transmission, said gauge's measurements are used in conventional stress wave formula to obtain results which are then correlated with the results of Formula II to estimate the load-bearing capacity of the pile.

In one preferred embodiment of the invention, the model pile apparatus further comprises a model pile, hammer weight, and dynamic measurement means provided on said model pile whereby the model pile is arranged to hold in a vertical position with its bottom end mounted to hold rigidly and its top end mounted in a manner to allow free vertical movement; the hammer weight being arranged to hit said model pile in a vertical, gravity-wise movement, and the dynamic measuring means being positioned accordingly to obtain measurements of said model pile depending on the manner of load impact of said hammer weight on said model pile and the manner of the load stress is distributed on said model pile.

In a preferred embodiment, the means for measuring strain exerted on said model pile are comprised of at least one gauge to measure at least one dynamic value mounted on the model pile at the distance, d, below and away from the load impact surface of said model pile's top end, wherein d is an appreciable distance in accordance with St. Venant's Principle. Preferably still, the distance d is at least one diameter of said model pile and, most preferably, is at least three times the greatest diameter of the load impact surface.

In another embodiment of the invention, the model pile is held in a vertical position within a frame. Preferably, the frame is provided with a foot mounting means at the base of said model pile and a means to hold the model pile's top end so that the model pile is held in a vertical position and in alignment for the hammer weight to strike. More preferably, the foot mounting means is provided in the form of a flat metal base with a screw-threaded hole at the centre to complementarily accommodate this screw-threaded base end of the model pile so that when the model pile is firmly held onto the flat metal base when it is screwed thereonto.

In yet another embodiment, the means to hold the top end of the model pile is comprised of a collar plate provided with a central aperture, the central aperture being fitted with a ball-bearing having an inner diameter that is marginally larger than the diameter of the model pile to allow said model pile to be inserted therethrough and allowing free vertical movement of the top end.

Preferably, the hammer weight is comprised of a ram, a guide means for directing the ram to hit top end surface of the model pile and means to dampen the ram's impact on the top end surface. Preferably still, the ram guide means further comprises a guiding rod which lower end is threaded to screw into a complementary threaded screw hole provided on the model pile's top end surface, the ram being provided with a complementary bore hole which enables said ram to slide through said guiding rod, and the damping means further comprises a cushioning disk to dampen and transmit the ram's impact onto the model pile.

BRIEF DESCRIPTION OF THE DRAWINGS

The method and apparatus of the present invention of estimating pile capacity will now be described in fuller detail with references to the following drawings as specific examples or illustrations which are not to be construed as delimiting the scope of the invention and the various other embodiments the invention is capable of.

LIST OF DRAWINGS

Figure 1:
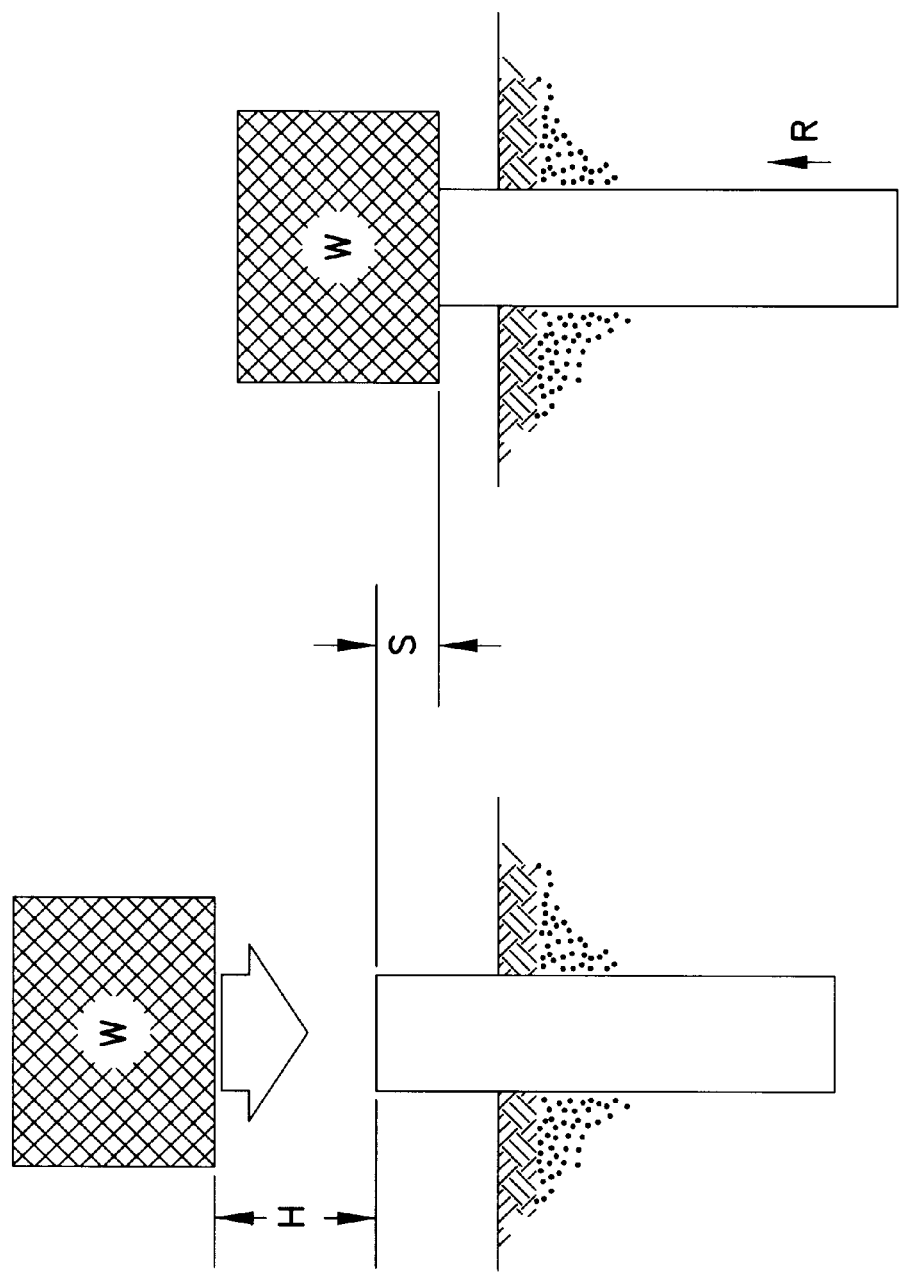

FIG. 1—shows the a physical representation of the Basic Dynamic Formula (described hereinbefore in the Background of Invention).

Figure 2A:
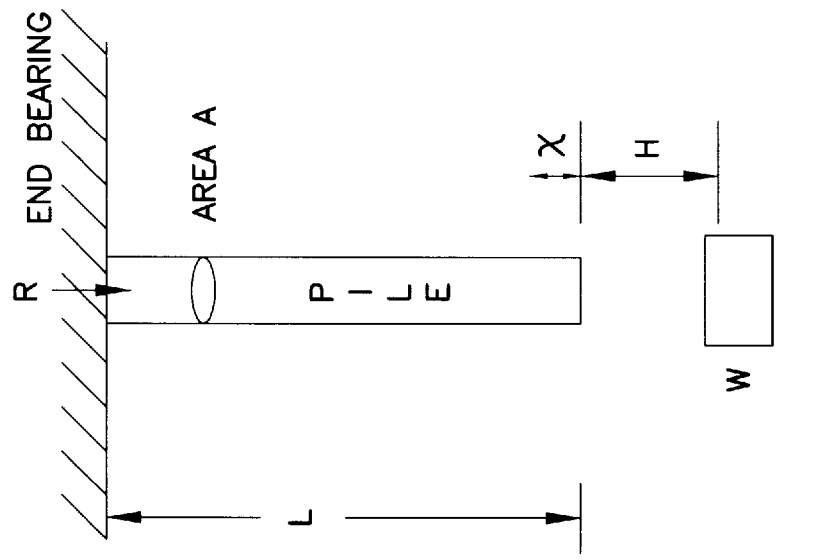
Figure 2B:
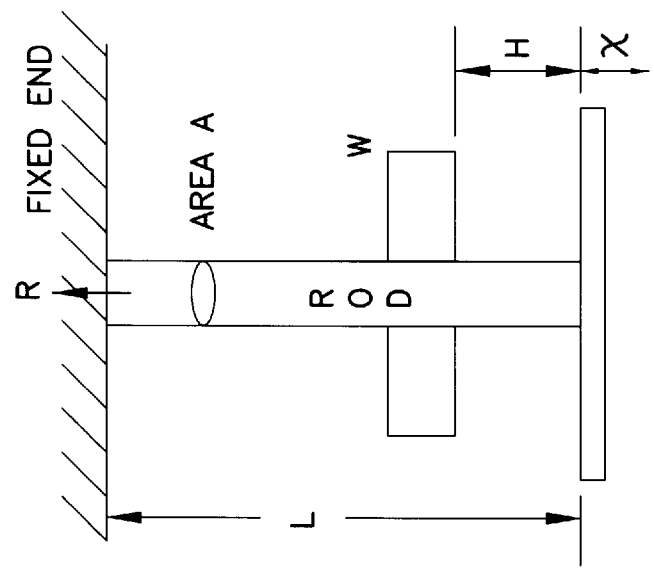

FIGS. 2A & 2B—compare in analogy the model based on the Impact Load Formula (FIG. 2A) with the inverted model of the conventional Pile Driving Formula (FIG. 2B).

Figure 3:
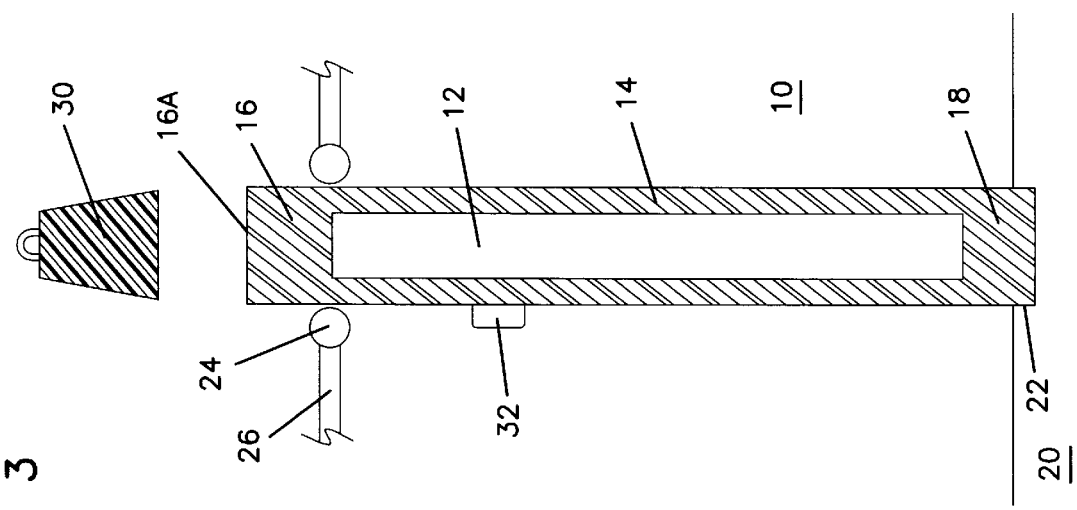

FIG. 3—shows the basic elements of a scaled-down model pile apparatus based on the method of the present invention.

Figure 4:
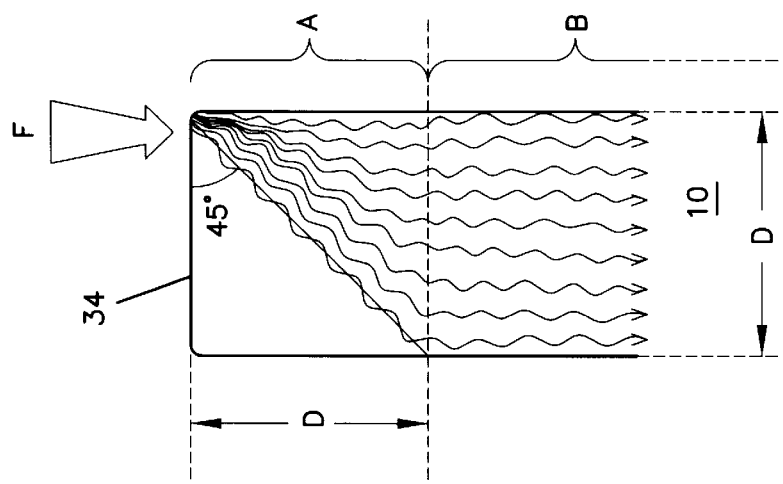

FIG. 4—shows a stress wave propagation and transmission pattern in a pile.

Figure 5:
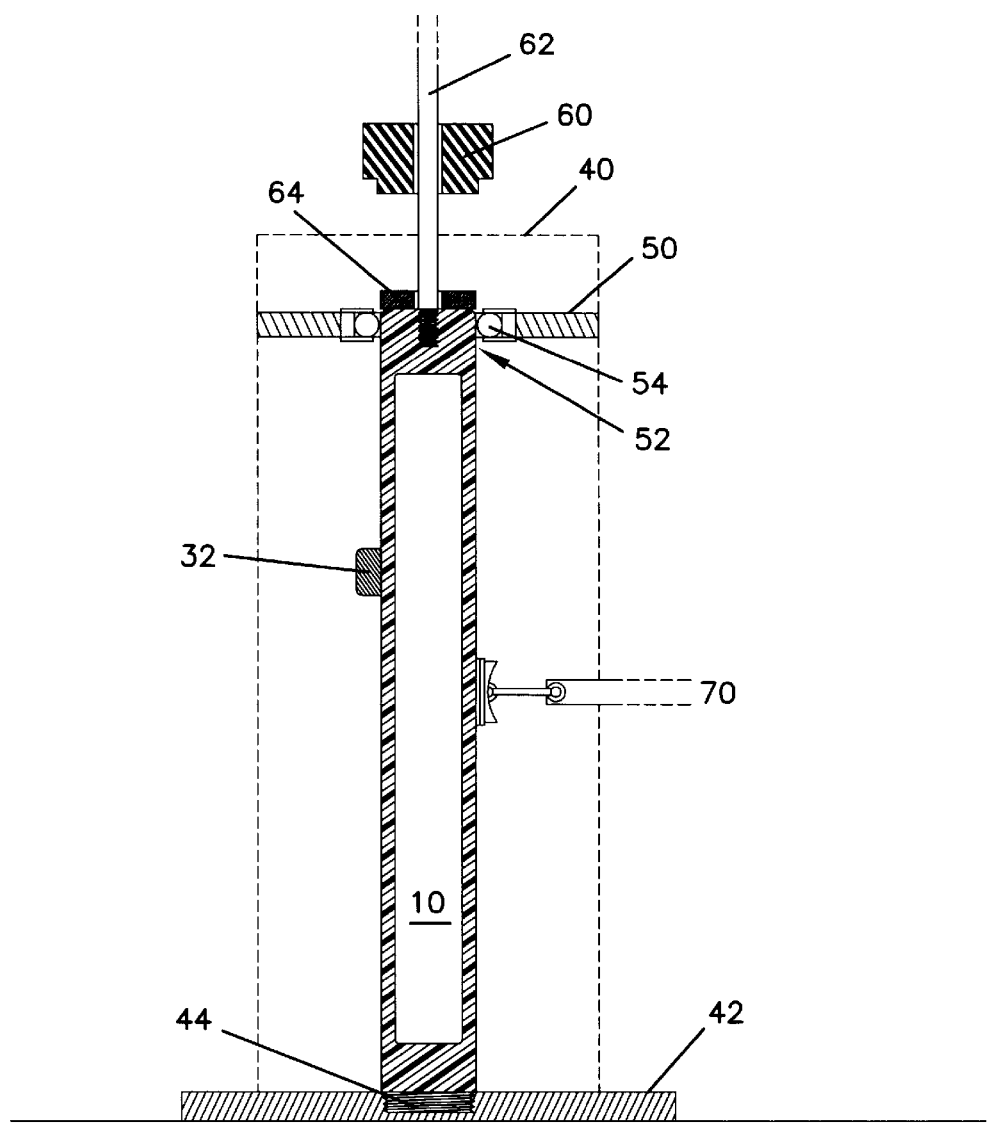

FIG. 5—shows a preferred embodiment of the model pile apparatus.

Figure 6:
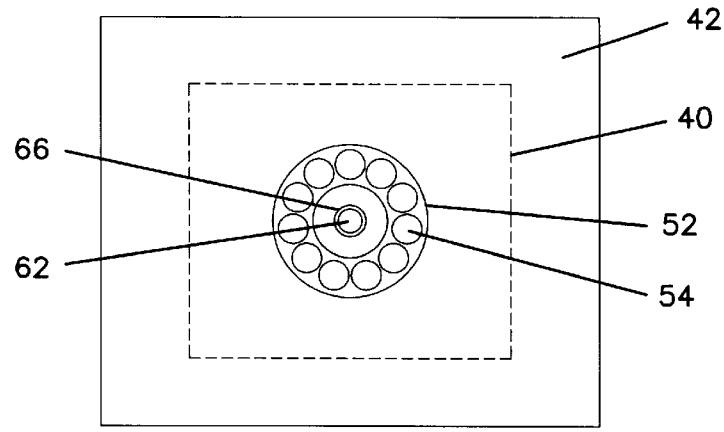

FIG. 6—shows a cross section of the apparatus of FIG. 5 in top plan view.

Figure 7A:
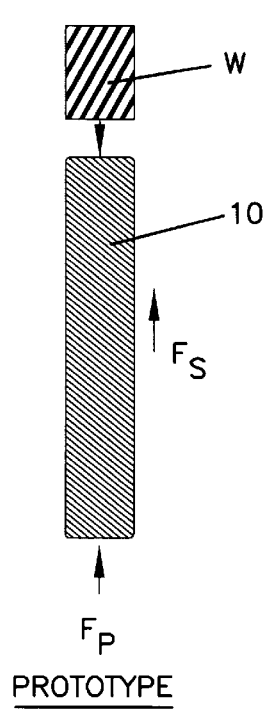
Figure 7B:
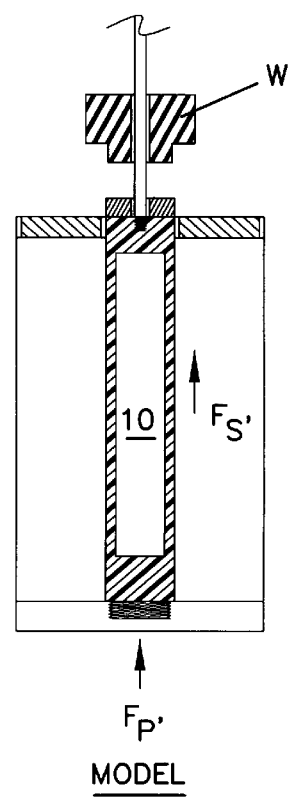

FIGS. 7A & 7B—shows diagrammatically the factors involved with respect to the prototype pile, FIG. 7A, and model pile, FIG. 7B, calculations disclosed in Example 5.

DETAILED DESCRIPTION OF THE PREFERRED EMBODIMENTS

The present invention discloses a method for estimating the load-bearing of a pile. The method comprising the steps of—

(a) constructing a scaled-down model pile apparatus which has been reduced to a size that may be accommodated within an indoors facility according to a calculated scaled-down ratio;

(b) subjecting said model pile apparatus to impact load tests to obtain dynamic measurements; and (c) correlating the dynamic measurements from said tests to said pile, to estimate the load-bearing of the pile. The Correlation Steep using a formula derived from the impact load theory.

The formula employed in the present invention is the Impact Load Formula that is commonly used in the structural analysis, such as a rod, based on the Impact Load Formula which may be obtained from any literature on structural analysis [e.g. from G. H. Ryder (1969), *Strength of Materials*, 3rd ed., p. 9], herein incorporated by reference, as Formula I as follows:

$$P = W\left[1 + \sqrt{1 + \frac{2hAE}{WL}}\right] \quad \text{Formula I}$$

wherein $P$ = impact load on rod, tonnes;

$W$ = weight of impact mass, equivalent to weight of ram, tonnes;

$h$ = stroke, m;

$L$ = length of rod, m;

$A$ = cross sectional area of rod, m$^2$;

$E$ = Young's modulus of rod, tonnes/m$^2$;

It could be seen from FIG. 2A that the Impact Load model is analogous to the Pile Driving model of FIG. 2B when the latter is inverted.

In the pile driving analysis, 1 to 2% of the ram weight, W, is sufficient to drive the pile to achieve the desired load-bearing capacity, R, hence, $$R \approx 100W$$

therefore Formula I may now be re-written as $$100W \Leftrightarrow W\left[1 + \sqrt{1 + \frac{2hAE}{WL}}\right]$$

As the {2hAE/WL} portion is the dominant factor in the equation, the relationship may be simplified into:

$$100W \Leftrightarrow W\sqrt{\frac{2hAE}{WL}}$$

Substituting 100W as the end-bearing, R:

$$\therefore R = W\sqrt{\frac{2hAE}{WL}} \Leftrightarrow \sqrt{\frac{2AEWh}{L}} \quad \text{Formula II}$$

A preferred embodiment of the method of the present invention is to substitute Formula I with Formula II as provided above wherein $R$ = soil resistance load or end-load bearing, tonnes;

$h$ = stroke, m;

$A$ = cross sectional area pile, m$^2$;

$E$ = Young's modulus of pile, tonnes/m$^2$;

$L$ = length of pile, m;

$W$ = weight of impact mass, equivalent to weight of ram, tonnes.

In a preferred embodiment of the method of the present invention, the scaled-down model pile apparatus, in its basic configuration, further comprises a model pile and hammer weight which is arranged to strike the model pile. The model pile is provided with (i) means to gauge the strain exerted on said model pile upon being hit by the hammer weight, and (ii) means to measure the velocity of the stress wave transmission. The gauge's measurements are used in conventional stress wave formula to obtain results which are then correlated with the results of Formula II to estimate the load-bearing capacity of the pile.

Several methods of stress wave transmission may be used. A wide selection of suitable wave equation may be found at the Internet website entitled "The Wave Equation Page for Piling" at http://www.geocities.com/CapeCanaveral/Hangar/2955. A major stress wave theory to analyse piles during driving and to estimate their static capacity is the Case Method (Goble, et. al., 1980). This method compared the pile force and velocity at a given time with a time 2L/c before that. The static and dynamic components are then separated one from another. This method is simple and can be readily applied in the field through the measurement of force and acceleration of the pile top using both strain gauges and accelerometers.

A more advanced method is the CAPWAP (Case Pile Wave Analysis Program) (Rausche, et. al., 1985). This technique uses similar instrumentation to the Case Method. The pile is divided up into a series of elements and the reflections from each are analysed based on their time of return to the pile top. A profile of the shaft resistance distribution is thus obtained.

It should be noted that the measurements obtained from the method of the present invention may be employed in most wave equation formula, not necessarily limited to the above two Case methods, to obtain the results for correlation purposes in estimating a pile's load-bearing capacity.

Scaled-down model for pile testing. Using the above method, either with Formula I or Formula II, a scaled-down model based on the Impact Load method may be built to test and predict the end load-bearing capacity of a prototype or actual pile to be used in pile-driving.

The model pile apparatus (described in detail hereinafter) may be scaled-down in accordance to a certain calculated ratio. It has been found that the method herein works for a ratio of actual:model in the range of x:1 where $1 \leq x \leq 100$. Representative of calculations to test the validity of specific ratios within the abovesaid range is given in the following, i.e. for the specific ratios of 60:1, 40:1 and 10:1.

EXAMPLE 1

Calculations for modelling ratio of 60:1

Standard values:

| | | |
|---|---|---|
| Pile modulus of mild steel, E | = | 2100 tonnes/cm² |
| Wave speed of mild steel, c | = | 5122 m/s |
| Specific weight of mild steel, SP | = | 7.85 tonnes/m³ |
| Yield strength for mild steel, y | = | 200 Mpa, |
| Modelling scale factor: actual:model = 60:1 | | |

Actual pile:

| | |
|---|---|
| Hammer type: | 7-tonne hydraulic hammer @ stroke of 1.2 m with efficiency of 75%. |
| Pile type: | 711 mm diameter × 12 mm thick stell pipe pile with length of 25 m. | factor of hammer and pile:

(Wh · eff) × (EA/L) = 139453 tons²
∴ load-bearing = 528.12 tons (with pile stress of about 200 MPa)

Model pile:

Hammer and pile/scale: (Wh · eff) × (EA/L)/3600 = 38.74 tons-m
[where the scale 3600 is obtain from 60²;

Calculations for modelling ratio of 60:1 p inidicates (actual) pile and m indicates model].
∴ load-bearing = 8.80 tons (1/60 × actual pile load-bearing)

$$R_p = \sqrt{2\left[\frac{AE \cdot Wh}{L}\right]_p} \; ; \; R_m = \frac{1}{60}R_p$$

$$\therefore 60R_m = \sqrt{2\left[\frac{AE \cdot Wh}{L}\right]_p}$$

$$\Rightarrow R_m = \sqrt{2\left[\frac{AE \cdot Wh}{L}\right]_p \cdot \frac{1}{60^2}}$$

1st Modelling attempt:

| Assumptions: | W | = | 0.08 tons = 80 kg |
|---|---|---|---|
| | h | = | 0.5 m |
| | eff | = | 0.75 |
| | L | = | 5.00 m |
| | load-bearing | = | 8.80 tons (about 100W) |
| Calculated: | A | = | 3.07 cm² |

Checking:

| Load-bearing, R | = | $\sqrt{\dfrac{2EA \times Wh \cdot eff}{L}}$ |
|---|---|---|
| | = | 8.80 tons; ∴OKAY! |
| Pile stress, st | = | R/A = 286 Mpa |
| | > | y = 200    ∴NOT OKAY |

2nd Modelling attempt:

| Use: | W | = | 0.06 tons = 60 kg |
|---|---|---|---|
| | eff | = | 0.75 m |
| | A | = | 3.07 cm² |
| | L | = | 3.50 m |
| Assumption: | h | = | 0.25 m |

Calculated:

load-bearing = 6.44 tons (about 100 W)

Checking:

| Load-bearing, R | = | $\sqrt{\dfrac{2EA\_Wh \cdot eff}{L}}$ |
|---|---|---|
| | = | 6.44; ∴OKAY! |
| Pile stress, st | = | R/A |
| | = | 209 Mpa |
| | ≅ | y = 200 ∴OKAY! |

EXAMPLE 2

Calculations for modelling ratio of 40:1

Standard values: - same as in Example 1 -
Modelling scale factor: actual:model = 40:1
Actual pile:

| | |
|---|---|
| Hammer type: | 7-tonne hydraulic hammer @ stroke of 1.2 m with efficiency of 75%. |
| Pile type: | 711 mm diameter × 12 mm thick steel pipe pile with length of 25 m. | factor of hammer and pile:

(Wh · eff) × (EA/L) = 139453 tons²
∴ load-bearing = 528.12 tons (with pile stress of about 200 MPa)

| Calculations for modelling ratio of 40:1 | | |
|---|---|---|
| Model pile: | | |
| Hammer + pile/scale: (Wh · eff) × (EA/L)/1600 = 87.16 tons-m | | |
| ∴ load-bearing | = | 13.20 tons (1/40 × actual pile load-bearing) |
| 1st Modelling attempt: | | |
| Assumptions: W | = | 0.12 tons = 120 kg |
| h | = | 0.3 m |
| eff | = | 0.75 |
| L | = | 3.00 m |
| load-bearing | = | 13.20 tons (about 100 W) |
| Calculated: A | = | 4.61 cm² |
| Checking: | | |
| Load-bearing, R | = | $\sqrt{\dfrac{2EA \times Wh \cdot eff}{L}}$ |
| | = | 13.20 tons; ∴OKAY! |
| Pile stress, st | = | R/A |
| | = | 286 MPa |
| | > | y = 200   ∴NOT OKAY |
| 2nd Modelling attempt: | | |
| Use: W | = | 0.09 tons = 90 kg |
| eff | = | 0.75 m |
| A | = | 4.61 cm² |
| L | = | 3.50 m |
| Assumption: h | = | 0.25 m |
| Calculated: | | |
| load-bearing | = | 9.66 tons (about 100 W) |
| Checking: | | |
| Load-bearing, R | = | $\sqrt{\dfrac{2EA \times Wh \cdot eff}{L}}$ |
| | = | 9.66 tons; ∴OKAY! |
| Pile stress, st | = | R/A |
| | = | 210 MPa |
| | ≅ | y = 200 ∴OKAY! |

EXAMPLE 3

| Calculations for modelling ratio of 10:1 | | |
|---|---|---|
| Standard values: - same as in Example 1 - | | |
| Modelling scale factor: actual:model = 10:1 | | |
| Actual pile: | | |
| Hammer type: | 7-tonne hydraulic hammer @ stroke of 1.2 m with efficiency of 75%. | |
| Pile type: | 711 mm diameter × 12 mm thick steel pipe pile with length of 25 m. | |
| factor of hammer and pile: | | |
| (Wh · eff) × (EA/L) | = | 139453 tons² |
| ∴ load-bearing | = | 528.12 tons (with pile stress of about 200 MPa) |
| Model pile: | | |
| Hammer and pile/scale: (Wh · eff) × (EA/L)/100 = 1394.53 tons-m | | |
| ∴ load-bearing | = | 52.81 tons (1/10 × actual pile load-bearing) |
| 1st Modelling attempt: | | |
| Assumptions: W | = | 0.50 tons = 500 kg |
| h | = | 0.5 m |
| eff | = | 0.75 |
| L | = | 5.00 m |
| load-bearing | = | 52.81 tons (about 100 W) |
| Calculated: A | = | 17.71 cm² |
| Checking: | | |
| Load-bearing, R | = | $\sqrt{\dfrac{2EA \times Wh \cdot eff}{L}}$ |
| | = | 52.81 tons; ∴OKAY! |
| Pile stress, st | = | R/A |
| | = | 298 MPa |
| | > | y = 200   ∴NOT OKAY |
| 2nd Modelling attempt: | | |
| Use: W | = | 0.40 tons = 400 kg |
| eff | = | 0.75 m |
| A | = | 17.71 cm² |
| L | = | 5.00 m |
| Assumption: h | = | 0.30 m |
| Calculated: | | |
| load-bearing | = | 36.59 tons (about 1% of bearing) |
| Checking: | | |
| Load-bearing, R | = | $\sqrt{\dfrac{2EA \times Wh \cdot eff}{L}}$ |
| | = | 36.59 tons; ∴OKAY! |
| | ≅ | mD = 0.07257) ∴OKAY! |
| Pile stress, st | = | R/A |
| | = | 206 MPa |
| | ≅ | y = 200 ∴OKAY! |

Those skilled in the art will recognize from the above calculation examples of specific ratios that further calculations may be able to confirm that the method will similarly work for other modelling factors, particularly in the range of x:1 where x ≧ 1.

It would also be apparent that when the size of the model is too small, i.e. where x is too large, it would be difficult to fix the strain gauge or other devices for measuring the strain exerted on the pile, or for directly measuring stress sustained by the pile. (Conventionally, strain gauges are used to measure strain exerted on the pile. Strain measurements are then converted to stress measurements).

Preferably, the ratio is x:1 where x is in the range of 100 ≧ x ≧ 1. Most preferably, the optimum ratio is 25:1 so that a length of the pile model and the hammer may be set up in an indoors facility such as in a typical factory building with a ceiling height of 8 m or higher. The following Example 4 shows the calculations to test the validity of the specific ratio of 25:1.

EXAMPLE 4

| Calculations for modelling ratio of 25:1 | |
|---|---|
| Standard values: - same as in Example 1 - | |
| Modelling scale factor: actual:model = 25:1 | |
| Actual pile: | |
| Hammer type: | 7-tonne hydraulic hammer @ stroke of 1.2 m with efficiency of 75%. |
| Pile type: | 711 mm diameter × 12 mm thick steel pipe pile with length of 25 m. |

-continued

Calculations for modelling ratio of 25:1 factor of hammer and pile:

$(Wh \cdot eff) \times (EA/L)$ = 139453 ton$^2$
∴ load-bearing = 528.12 tons (with pile stress of about 200 MPa)

Model pile:

Hammer and pile/scale: $(Wh \cdot eff) \times (EA/L)/100$ = 223.12 tons-m
∴ load-bearing = 21.12 tons (1/25 × actual pile load-bearing)

1st Modelling attempt:

| Assumptions: | W | = | 0.20 tons = 200 kg |
| | h | = | 0.5 m |
| | eff | = | 0.75 |
| | L | = | 5.00 m |
| | load-bearing | = | 21.12 tons (about 100 W) |
| Calculated: | A | = | 7.08 cm$^2$ |

Checking:

Load-bearing, R = $\sqrt{\dfrac{2EA \times Wh \cdot eff}{L}}$

= 21.12 tons; ∴OKAY!
Pile stress, st = R/A
                = 298 MPa
                > y = 200   ∴NOT OKAY 2nd Modelling attempt:

| Use: | W | = | 0.15 tons = 150 kg |
| | eff | = | 0.75 m |
| | A | = | 7.08 cm$^2$ |
| | L | = | 5.00 m |
| Assumption: | h | = | 0.30 m |
| Calculated: | | | |
| | load-bearing | = | 14.17 tons (about 100 W) |

Checking:

Load-bearing, R = $\sqrt{\dfrac{2EA \times Wh \cdot eff}{L}}$

= 14.17 tons; ∴OKAY!
Pile stress, st = R/A
                = 200 MPa
                ≅ y = 200 ∴OKAY!

Apparatus

The application of the method of the present invention involves the construction of a scaled-down model pile apparatus which will be disclosed hereinafter.

The essential elements of a model pile apparatus for use in the method of the present invention for estimating the load-bearing of a pile comprises (i) a model pile, (ii) hammer weight, and (iii) dynamic measurement means provided on said model pile. The structural relationship between each of these three elements is characterised in that the model pile is arranged to hold in a vertical position with its bottom end mounted to hold rigidly and its top end mounted in a manner to allow free vertical movement;

the hammer weight is arranged to hit said model pile in a vertical, gravity-wise movement, and the dynamic measuring means are positioned accordingly to obtain measurements of said model pile depending on the manner of load impact of said hammer weight on said model pile and the manner of the load stress is distributed on said model pile.

FIG. 3 illustrates the basic or fundamental configuration of the scaled-down model pile apparatus wherein the model pile (10) may be provided in the form of a steel pipe pile with hollow bore (12) and having a cylindrical wall (14) of known thickness (which is 12 mm in the above Examples 1 to 4). In this instance, the model pile's (10) both ends (16, 18) are provided with solid ends. The model pile (10) is arranged to hold in a vertical position wherein the bottom end (18) is mounted to hold rigidly on a solid floor or ground (20) ideally to achieve a 100% end load-bearing by the model pile (10) upon impact by the drop of the hammer weight (30).

On the other hand, the top end (16) of the model pile (10) is mounted in a manner to allow free vertical movement but rigidly against any horizontal movement. In this manner, the force exerted by the dropping of the hammer weight will translate into vertical stress or compression with no or minimal loss of force via horizontal or lateral movement of the model pile.

As shown in FIG. 3, the bottom end's (18) ideal 100% end load-bearing may be attempted by having the end (18) lodged in a depression (22) complementing the diameter of the bottom end (18) and holding said end in a rigid manner against any lateral movement along the ground (20). In this configuration, it will be understood that the solid ground (20) must be hard enough to withstand the impact of the hammer weight's drop on the model pile (10) so that the end load-bearing of the pile may be achieved as ideally as possible.

The top end (16) as shown in FIG. 3 is held by means (24, 26) that allow frictionless or minimal friction of vertical movement of the model pile while preventing any lateral or horizontal movement. For example, such means could be provided in the form of ball-bearing or roller means (24) that allows unfettered vertical movement of the pile while some rigid frame, arm or collar (26) may be provided to hold the ball-bearing or roller means (24) in place or to enable the means (24) to be mounted securely and rigidly thereon to prevent lateral movement of the pile (10).

The hammer weight (30) is arranged to hit said model pile (10) in a vertical, gravity-wise movement so that the force of the drop is fully transmitted into vertical stress force on the model pile (10).

The measurement means (32) are positioned accordingly to obtain measurements of the dynamics of said model pile (10) when hit by the hammer weight (30). The position of the mounting of the dynamic measurement means (32) on the model pile (10) depends on the manner of load impact of said hammer weight when dropped to hit the top end (16) of said model pile (10), and on the manner of the load stress generated from the drop is distributed on said model pile (10).

In one embodiment of the invention, the means for measuring (32) the dynamics of the model pile (10) due to stress exerted thereon are comprised of at least one gauge to measure at least one dynamic value mounted on the model pile at a distance, d, below and away from the load impact surface of said model pile's top end.

The ideal distance to place the measuring means (32) may be adopted from the conventional wisdom of structural engineering, for example, d may be an appreciable distance in accordance with St. Venant's Principle [Ryder, ibid., p. 2].

If one may have recourse to conventional theories on wave transmission and propagation of impact or stress in elongated solids, then 45° (from the horizontal plane of incident) may be taken as the degree of propagation of the stress wave from one edge of an elongated solid body before the stress becomes uniformly transmitted along the rest of the elongation as shown in FIG. 4. In this figure, the impact of force (F) on one edge of the pile (10) with diameter, d, imparts stress which is propagated (A) at 45° from the horizontal plane (34) before the stress distribution becomes uniform (B) after a distance that is at least one diameter of said model pile.

A preferred distance is at least three times the greatest diameter or width of the load impact surface (34) so that no appreciable error will be introduced.

The basic configuration of a model pile apparatus of the present invention as shown in FIG. 3 may be further configured in various preferred embodiments to enhance on each of the first two features of (i) arranging the model pile to hold in a vertical position with its bottom end mounted to hold rigidly and its top end mounted in a manner to allow free vertical movement and (ii) arranging the hammer weight to hit said model pile in a vertical, gravity-wise movement.

For example, the holding means (24, 26) (which rigidly holds the model pile (10) against any lateral movement yet allow free vertical movement) may be provided with a frame (40) which substantially houses the model pile (10) as shown in FIG. 5 so that the holding means (24, 26) may be held in place to support the pile's top end whereby the model pile is held in a vertical position and in alignment for the hammer weight to strike. The arrangement of the example of the apparatus in FIG. 5 is shown in top plan view in FIG. 6.

A still preferred embodiment is to provide the frame (40) with a base (42) so that the frame-base (40, 42) structure substantially houses and holds the model pile (10) in accordance with the requirements of vertically-fixed bottom end and vertically-free top end of the model pile (10).

It would be apparent that the base (42) should be made of material of sufficient hardness to withstand the impact transmitted from the hammer weight (30) down the model pile (10) onto the base (42). A good example is a piece of mild steel plate of sufficient thickness whereupon may be fabricated means to mount the bottom edge of the frame (40) onto said plate.

Preferably still, a foot mounting means (44) at the base (42) of frame (40) is provided to hold the bottom end of the model pile (10) rigidly in place in the same manner of a complementary depression (22) described in FIG. 3. It would be apparent to the skilled person that many forms of conventionally mounting the foot or bottom end (18) of the model pile (10) may be equally effective, for example, clamping or bracing means, nut and/or bolting means, welding, and screw-thread means.

The most preferred method to mount the bottom end (18) of the pile currently envisaged is to provide the foot mounting means (44) on the flat metal base plate (42) with a screw-threaded hole at the centre which will complementarily accommodate the screw-threaded base end (18) of the model pile (10) so that the model pile (10) may be firmly held onto the flat metal base plate (42) when it is screwed into the threaded foot mounting means (44).

In one preferred embodiment of the model pile apparatus of the present invention, the means for holding the top end of the model pile may be provided as a collar plate (50) wherein its centre is provided with a central aperture (52). The central aperture (52) may be fitted with roller means (24) to hold the top end (16) of the model pile (10) in position against lateral movement but allowing unrestricted vertical movement. Preferably still, the central aperture (52) is fitted with a ball-bearing means (54) having an inner diameter is marginally larger than the diameter of the model pile so that the said model pile (10) may be inserted therethrough and allowing free vertical movement of the top end (16) of the model pile (10).

In another preferred embodiment of the invention, the hammer weight (30), used for hammering the top end surface (16A) of the model pile (10) to produce the impact loading and stress, is provided with means to guide the drop of the hammer weight so that it hits flatly and centrally on the top end surface (16A) in order to impact the top end (16) in a uniform manner.

Preferably still, hammer weight (30) comprises a ram (60), a guide means (62) for directing the ram (60) to hit top end surface (16A) of the model pile (10) and means (64) for dampening the ram's (60) impact on the top end surface (16A).

Those skilled in the art will recognize to provide for the hammer weight, the guide means and damping effect; for example the guide means may be provided as a cylindrical tube which inner diameter is marginally larger than the model pile and the ram so that the ram is guided by the cylindrical tube when dropped in the manner of a piston head to hit the top end surface of the model pile.

Preferably, the ram is made from high tensile steel with a central bore (66) and the guide means (62) is a guiding rod with a diameter that is marginally smaller than the central bore (66) so that the rod (62) may be inserted through ram (60) via the central bore (66).

The rod (63) may be affixed onto the top end surface (16A) of the model pile at a central location so that when dropped, it is guided by the rod (62) to centrally hit the top end surface (16A) of the model pile (10). Preferably, the guiding rod (62) is affixed to the top end surface (16A) by screw and thread means, e.g. by providing the lower end of the guiding rod (62) with threading and by further providing the centre of the top end surface (16A) with a complementary pit with screw threading so that the guiding rod (62) may be affixed onto the top end surface (16A) by screwing fit thereinto.

A further preferred embodiment is to provide means to dampen the impact of the ram upon hitting the top end surface (16). An example of such damping means is a cushioning disk (64), preferably made of an elastic material which may ideally dampen the impact and fully transmit the force of the impact without loss of energy. Practically, rubber may be used to make the cushioning disk which is provided with a central bore to fit through the guiding rod (62).

Materials used to fabricate each of the above described components of the model pile apparatus may be selected from a wide variety of conventional materials commonly available, depending on the function of the particular component and whether handling is required. For example, the frame (40) may be fabricated from aluminium which is light yet strong enough for the purpose so that the frame is light enough to be removed when necessary, for example, to change the model pile (10) to a different model, yet is strong enough to securely and rigidly hold the collar plate.

Similarly, the guiding rod (62) may also be made of aluminium to facilitate ease of unscrewing from the top end surface (16A) to remove the model pile. On the other hand, components such as the ram is preferably fabricated from high tensile steel to withstand the force of the impact of drop hammering. The base (42) holding the bottom end (18) of the model pile (10), depending on the thickness of the base, may be made of mild steel, for example.

Various other accessories, variations or adaptations may be added to the model pile apparatus described above. For example, the frame (40) may be designed in such way to allow soil to be filled therein and compacted to a required density to simulate that actual soil conditions found by soil investigation works at the construction site so that model pile surface or skin friction may be measured during hammering.

Alternatively, friction pads (70) may designed in a way analogous to the principles of the brake or clutch mechanism of automobiles to provide for controlled friction to the surface of the model pile to simulate skin friction on the actual or prototype pile by the site's actual soil conditions during piling. The working mechanism of such friction pads may be designed and built by a person skilled in the art and such mechanism is capable of variations which are too numerous to be described herein.

Industrial application

Using the following example, based on FIGS. 7A and 7B, it will now be shown how the pile driving model apparatus described above may be applied industrially in the foundation design of an actual or prototype pile.

EXAMPLE 5

An application in foundation pile design
Model pile-and-hammer's dimensions:

| | | |
|---|---|---|
| Ram weight, W | = | 0.15 tonnes |
| Stroke, h | = | 0.30 meter |
| Hammer efficiency, eff | = | 0.75 |
| Pile area, A | = | 7.07 cm$^2$ |
| Pile modulus, E | = | 2100.00 tonnes/cm$^2$ |
| Pile length, L | = | 5.00 meters |
| Calculated Resistance for model pile, R$_{model}$ | = | $\sqrt{\dfrac{2EA \times Wh \cdot eff}{L}}$ |
| | = | 14.16 tonnes. |

Ideal pile (i.e. 100% end load-bearing):

Selection of hammer, pile and soil system:-
   hammer type: 7-tonne hydraulic hammer @ stroke of 1.2 m with efficiency of 75%.
   pile type: 711 mm diameter × 12 mm thick steel pipe with length of 25 m.
   soil type: refer to soil investigation report.
Skin friction, F$_s$, calculated from soil investigation report
   = 0 tonne/m$^2$
End load-bearing, F$_p$, calculated from soil investigation report
   = 500 tonnes
Total load bearing of pile, F$_t$ = F$_s$ + F$_p$
   = 500 tonnes + 0 tonne
   = 500 tonnes.

| | | |
|---|---|---|
| Ram weight, W | = | 7.00 tonnes |
| Stroke, h | = | 1.20 meter |
| Hammer efficiency, eff | = | 0.75 |
| Pile area, A | = | 263.50 cm$^2$ |
| Pile modulus, E | = | 2100.00 tonnes/cm$^2$ |
| Pile length, L | = | 25.00 meters |

Resistance for prototype/actual pile,
   R$_{prototype}$ = $\sqrt{\dfrac{2EA \times Wh \cdot eff}{L}}$
   = 528.10 tonnes
   > 500 tonnes of designed bearing; ∴OKAY!

Scaled-down ratio of 1:χ
   R$_{model}$: R$_{prototype}$
   14.16: 528.10
   1: 37.30 ≅ 1:37; therefore χ = 37

Practical or Actual pile (i.e. with skin friction & end load-bearing combination)

Selection of hammer, pile and soil system:-
   hammer type: 7-tonne hydraulic hammer @ stroke of 1.2 m with efficiency of 75%.
   pile type: 711 mm diameter × 12 mm thick steel pipe with length of 25 m.
   soil type: refer to soil investigation report.
Unit skin friction, F$_s$, calculated from
   soil investigation report = 6.5 tonne/m$^2$
∴ Total skin friction of the pile, F$_s$ = 363 tonnes
   ≅ 360 tonnes
End load-bearing calculated from = 150 tonnes
soil investigation report, F$_p$
Total load bearing of pile, F$_t$ = F$_s$ + F$_p$
   = 500 tonnes + 0 tonne

| | | |
|---|---|---|
| Ram weight, W | = | 7.00 tonnes |
| Stroke, h | = | 1.20 meter |
| Hammer efficiency, eff | = | 0.75 |
| Pile area, A | = | 263.50 cm$^2$ |
| Pile modulus, E | = | 2100.00 tonnes/cm$^2$ |
| Pile length, L | = | 25.00 meters |

Resistance for actual
or prototype pile, R$_{prototype}$ = $\sqrt{\dfrac{2EA \times Wh \cdot eff}{L}}$ = 528.10 tonnes Question (based on Impact Load Analogy theory): is the design okay?
Checking:

Scaled-down ratio of 1:χ
   R$_{model}$: R$_{prototype}$
   14.16: 528.10
   1: 37.30 ≅ 1:37; therefore χ = 37
Measured skin friction for model pile = 9.73 tons (F$_s$/χ)

$$F_{p'} > \frac{F_p}{\chi} \Rightarrow F_p'$$

> 4.05 tonnes.
∴ Design is okay!

From the above description on the general working principles of the invention and the specific embodiments thereof, it would be obvious to a person skilled in the art that there are many variations and alternative embodiments that may be used in substitution of the steps or processes of the present invention's method, and many of the various parts, components or alternative embodiments not specifically described herein may be used in substitution of the corresponding elements of the method and apparatus of the present invention.

For instance, there are various mathematical methods that may be used to arrive at different formulas derived from the original Impact Load Formula (Formula 1) and such derived formulas may be equally applicable in the method of the invention and in the use of the apparatus hereof. The model pile apparatus described herein, too, has many possibilities of alternate parts or materials that may be used as substitutes to effectively employ the working principles thereof. These embodiments are not to be considered as departures from the present invention as illustrated by the examples and specific embodiments described herein and shall be considered as falling within the letter and spirit of the following claims.

What is claimed is:

1. A method for estimating the load-bearing of a pile comprising—

(a) constructing a scaled-down model pile which has been reduced to a size accomodable within an indoors facility according to a calculated scaled-down ratio, wherein said model pile is held vertically against horizontal movement with its bottom end mounted rigidly against vertical movement and its top end mounted to allow free vertical movement;

(b) subjecting said model pile to impact load tests to obtain dynamic measurements; and (c) correlating the dynamic measurements from said tests to said pile.

2. A method according to claim 1 wherein the correlation step (c) uses a formula derived from the impact load theory.

3. A method according to claim 2 wherein the Impact Load Formula is:

$$P = W\left[1 + \sqrt{1 + \frac{2hAE}{WL}}\right] \quad \text{Formula I}$$

wherein $P$ = impact load on pile, tonnes;

$W$ = weight of impact mass, equivalent to weight of ram, tonnes;

$h$ = stroke, m;

$L$ = length of pile, m;

$A$ = cross sectional area of rod = cross sectional area pile, $m^2$;

$E$ = Young's modulus of rod = Young's modulus of pile, tonnes/$m^2$.

4. A method according to claim 3 wherein the derived Formula I used is $$R = \sqrt{\frac{2AEWh}{L}} \quad \text{Formula II}$$

wherein $R$ = soil resistance load or end load-bearing, tonnes;

$h$ = stroke, m;

$A$ = cross-sectional area pile, $m^2$;

$E$ = Young's modulus of pile, tonnes/$m^2$;

$L$ = length of pile, m;

$W$ = weight of impact mass, equivalent to weight of ram, tonnes.

5. A method according to claim 3 wherein the scaled-down ratio of prototype:model is x:1 wherein $x \geq 1$.

6. A method according to claim 5 wherein the ratio is 25:1.

7. A method according to claim 3 wherein the scaled-down model pile apparatus further comprises a model pile and hammer weight, said model pile being provided with (i) means to gauge the strain exerted on said model pile upon being hit by the hammer weight, and (ii) means to measure the velocity of the stress wave transmission, said strain gauge's measurements are used in conventional stress wave formula to obtain results which are then correlated with the results of Formula II to estimate the load-bearing capacity of the pile.

8. A model pile apparatus for use in a method for estimating the load-bearing capacity of a pile, said model pile apparatus comprising a model pile, hammer weight, and dynamic measurement means provided on said model pile, wherein the model pile being arranged to hold vertically against horizontal movement with its bottom end mounted to hold rigidly against vertical movement and its top end mounted in a manner to allow free vertical movement;

the hammer weight being arranged to hit the top end surface of said model pile in a vertical, gravity-wise movement, and the dynamic measuring means being positioned accordingly to obtain measurements of said model pile depending on the manner of load impact of said hammer weight on said model pile and the manner of the load stress is distributed on said model pile.

9. A model pile apparatus according to claim 8 wherein the means for measuring strain exerted on said model pile are comprised of at least one gauge to measure at least one dynamic value mounted on the model pile at the distance, d, below and away from the load impact surface of said model pile's top end, wherein d is at least the distance in accordance with St. Venant's Principle.

10. A model pile apparatus according to claim 9 wherein the distance d is at least one diameter of said model pile.

11. A model pile apparatus according to claim 10 wherein the distance d is at least three times the diameter of the load impact surface.

12. A model pile apparatus according to claim 8 wherein the model pile is held in a vertical position within a frame.

13. A model pile apparatus according to claim 12 wherein the frame is provided with a foot mounting means at the base of said model pile and a means to hold the model pile's top end so that the model pile is held in a vertical position and in alignment for the hammer weight to strike.

14. A model pile apparatus according to claim 13 wherein the foot mounting means is provided in the form of a flat metal base with a screw-threaded hole at the centre to complementarily accommodate the screw-threaded base end of the model pile so that when the model pile is firmly held onto the flat metal base when it is screwed thereonto.

15. A model pile apparatus according to claim 13 wherein the means to hold the top end of the model pile is comprised of a collar plate provided with a central aperture, the central aperture being fitted with a ball-bearing having an inner diameter that is marginally larger than the diameter of the model pile to allow said model pile to be inserted therethrough and allowing free vertical movement of the top end.

16. A model pile apparatus according to claim 13 wherein the hammer weight is comprised of a ram, a guide means for directing the ram to hit top end surface of the model pile and means to dampen the ram's impact on the top end surface.

17. A model pile apparatus according to claim 15 wherein the ram guide means further comprises a guiding rod which lower end is threaded to screw into a complementary threaded screw hole provided on the model pile's top end surface, the ram being provided with a complementary bore hole which enables said ram to slide through said guiding rod, and the damping means further comprises a cushioning disk to dampen and transmit the ram's impact onto the model pile.

18. A model pile apparatus according to claim 8 for use in a method for estimating the load-bearing of a pile comprising:

(a) constructing a scaled-down model pile apparatus which has been reduced to a size that may be accommodated within an indoors facility according to a calculated scaled-down ratio;

(b) subjecting said model pile apparatus to impact load tests to obtain dynamic measurements; and (c) correlating the dynamic measurements from said tests to said pile.

19. A pile driven into the soil wherein the pile's load-bearing capacity has been estimated by with the method according to claim 1.

20. A pile according to claim 19 wherein the pile's load-bearing capacity has been estimated using a model pile apparatus according to claim 8.

* * * * *